(12) United States Patent
Kim et al.

(10) Patent No.: US 7,569,102 B2
(45) Date of Patent: *Aug. 4, 2009

(54) WET TYPE AIR CLEANER

(75) Inventors: Woong Kim, Seoul (KR); Seok Hee Lee, Seoul (KR)

(73) Assignee: Daewoo Electronics Corporation, Seoul (KR)

( * ) Notice: Subject to any disclaimer, the term of this patent is extended or adjusted under 35 U.S.C. 154(b) by 681 days.

This patent is subject to a terminal disclaimer.

(21) Appl. No.: 11/268,704

(22) Filed: Nov. 8, 2005

(65) Prior Publication Data

US 2006/0096461 A1  May 11, 2006

(30) Foreign Application Priority Data

Nov. 8, 2004  (KR) ...................... 10-2004-0090600

(51) Int. Cl.
*B01D 47/00* (2006.01)
(52) U.S. Cl. ............................. 96/281; 96/283; 96/284; 96/286
(58) Field of Classification Search ................... 96/283, 96/285, 281, 284, 286; 95/218
See application file for complete search history.

(56) References Cited

U.S. PATENT DOCUMENTS

| | | | | |
|---|---|---|---|---|
| 2,053,647 A | * | 9/1936 | White | .......................... 261/91 |
| 3,358,413 A | * | 12/1967 | Kalika | .......................... 96/282 |
| 4,686,940 A | | 8/1987 | Fullemann | |
| 7,077,886 B2 | * | 7/2006 | Rosen | .......................... 95/218 |
| 2003/0005825 A1 | | 1/2003 | Hogan | |
| 2006/0096460 A1 | * | 5/2006 | Kim | .......................... 96/283 |

FOREIGN PATENT DOCUMENTS

| | | |
|---|---|---|
| CA | 907544 | 8/1972 |
| DE | 20312576 | 12/2003 |
| GB | 392909 | 5/1933 |
| GB | 904606 | 8/1962 |
| KR | 1994-5178 | * 3/1994 |

* cited by examiner

*Primary Examiner*—Duane Smith
*Assistant Examiner*—Ives Wu
(74) *Attorney, Agent, or Firm*—Bacon & Thomas, PLLC (57) ABSTRACT

A wet type air cleaner includes a purification unit which includes an inner guide portion for drawing a cleaning water upward, a water jetting nozzle for injecting the cleaning water drawn thereto through the inner guide portion, and a blower for drawing air downward. An outer guide portion is separately installed at an outside of the inner guide portion and with a gap therebetween to allow the air downwardly drawn by the blower and the droplets injected from the water jetting nozzle to flow into the cleaning water. The inner guide portion has a guide formed on its inner wall for upward drawing of the cleaning water and the outer guide portion has a guide formed on its inner walls for downward drawing of the air.

16 Claims, 5 Drawing Sheets

WET TYPE AIR CLEANER

FIELD OF THE INVENTION

The present invention relates to a wet type air cleaner; and, more particularly, to a wet type air cleaner capable of effectively removing noxious substances from air drawn into the air cleaner by way of directing the drawn air into cleaning water, while maximizing a contact between the air and the cleaning water.

BACKGROUND OF THE INVENTION

In general, an air cleaner is an apparatus for discharging clean air after removing contaminants from indoor air containing fine dusts, various noxious gases, various germs, molds, viruses, etc., by using a purification medium. Such an air cleaner can be used through all seasons because it has various functions of removing unpleasant odors and small particles such as ticks, pollen and furs of pets, preventing an outbreak of disease due to an aerial infection, and so forth as well as its principal function of maintaining indoor air clean and pleasant.

Air cleaners can be largely classified into two types: dry type and wet type. Dry type air cleaners can be divided again into a filter type and an electric dust collection type.

As for the filter type air cleaner since various fine particles are captured while air passes through filters, the filter type air cleaner exhibits a high purifying efficiency, and thus is adequate for use in a season in which yellow dust comes. However, since the filters need to be replaced periodically, maintenance cost is high. The dust collection type air cleaner employs an electric dust collecting plate instead of a filter, so it has a merit in that there is no need to replace filters. However, if dusts are accumulated on the electric dust collecting plate, purifying efficiency of the air cleaner will be deteriorated, and dust removing capacity thereof will also be undermined.

Meanwhile, a wet type air cleaner employs a method for making floating particles in introduced air deposited in water by allowing the introduced air to contact water. The wet type air cleaner removes fine particles and microbe in the air with an adsorbing effect of mist particles by using air containing fine liquid particles generated by finely spraying water, fine liquid particles being smaller than or equal to about 0.5 µm.

One of such wet type air cleaners is disclosed in Japanese Patent Laid-open Publication No. 2000-334240, entitled "WET TYPE AIR CLEANER".

The wet type air cleaner includes an air circulation passage through which air is introduced into the inside of the air cleaner and then is outputted to the outside after being purified and a reservoir containing liquid therein. The air cleaner further includes a blower unit for allowing the air to be circulated through the air circulation passage and a spray unit for spraying the liquid into a spray space in the air cleaner.

The blower unit includes a fan for drawing the air into the spray space and a motor for driving the fan. The spray unit includes a pump for pumping up the liquid from the reservoir and a nozzle for spraying the liquid into the spray space.

The air supplied into the air circulation passage typically flows downward after being introduced into the air cleaner from upside, whereas the liquid is sprayed upward from downside. Therefore, the air introduced into the air cleaner is brought into contact with fine liquid particles sprayed by the nozzle, thereby allowing noxious substances in the air to be adsorbed by the fine liquid particles.

In the conventional wet type air cleaners as described above, however, droplets adsorbing fine dust and dirt particles are discharged from the air cleaner together with purified air, thereby resulting in poor purification efficiency and an unexpected high humidity.

Further, the conventional wet type air cleaner has a drawback in that noise is increased by injecting water on an inner wall of the air cleaner to collect dusts or the like. Furthermore, in order to enhance the cleaning effect, a contact of the air containing dusts and the dispersed cleaning water needs to be increased. However, the contact between the cleaning water and the air is insufficient, so that the purification ability thereof is deteriorated.

SUMMARY OF THE INVENTION

It is, therefore, a primary object of the present invention to provide a wet type air cleaner capable of maximizing an air cleaning efficiency by way of increasing a contact between water particles and air.

It is another object of the present invention to provide a wet type air cleaner capable of effectively supplying and dispersing cleaning water by a centrifugal force.

In accordance with a preferred embodiment of the present invention, there is provided a wet type air cleaner, comprising: a housing provided with an air inlet and an air outlet and containing cleaning water therein; a motor having a rotation shaft to provide rotation force; and a purification unit fixedly installed to the rotation shaft, wherein the purification unit includes: an inner guide portion whose introduction is submerged into the cleaning water in the housing, for drawing upwardly the cleaning water, the inner guide portion having a guide formed on an inner wall of the inner guide portion for upward drawing of the cleaning water; a water jetting nozzle connected to an upper end of the inner guide portion for injecting the cleaning water drawn thereto through the inner guide portion; a blower installed at upper end of the water jetting nozzle, the blower having a fan for drawing air downward; and an outer guide portion separately installed at an outside of the inner guide portion with a gap therebetween to allow the air downwardly drawn by the blower and the droplets injected from the water jetting nozzle to flow into the cleaning water.

In accordance with another preferred embodiment of the present invention, there is provided a wet type air cleaner, comprising: a housing provided with an air inlet and an air outlet and containing cleaning water therein; a motor having a rotation shaft to provide rotation force; and a purification fixedly installed to the rotation shaft, wherein the purification unit includes: an inner guide portion whose introduction is submerged into the cleaning water in the housing, for upwardly drawing the cleaning water; a water jetting nozzle connected to an upper end of the inner guide portion for injecting the cleaning water drawn thereto through the inner guide portion; a blower installed at upper end of the water jetting nozzle, the blower having a fan for drawing air downward; an outer guide portion separately installed at an outside of the inner guide portion with a gap therebetween to allow the air downwardly drawn by the blower and the droplets injected from the water jetting nozzle to flow into the cleaning water, the outer guide portion having a guide formed on an inner wall thereof for downward drawing of the air from the blower.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENT

Hereinafter, preferred embodiments of the present invention will be described in detail with reference to the accompanying drawings.

Figure 1:
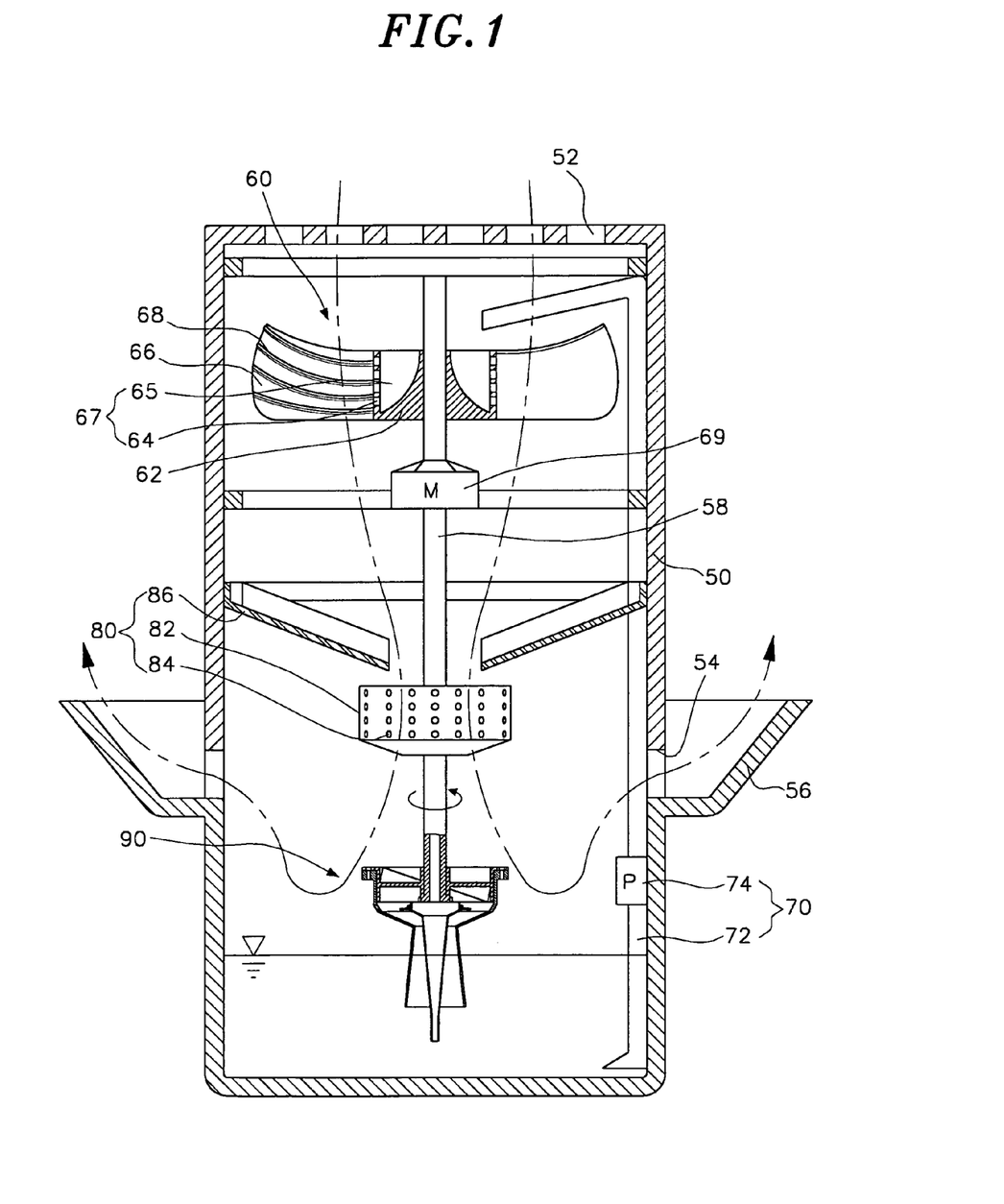
FIG. 1 shows a sectional view of a wet type air cleaner in accordance with the present invention.

Referring to FIG. 1, there is shown a sectional view of a wet type air cleaner in accordance with the present invention. As shown in FIG. 1, the wet type air cleaner includes a housing 50 provided with air inlets 52 and air outlets 54; a blower unit 60 installed below the air inlets 52; a water supply unit 70 for supplying cleaning water contained in the housing 50 into the blower unit 60; a sprinkling unit 80 installed below the blower unit 60; and an purification unit 90 installed below the sprinkling unit 80.

The housing 50 is of a cylindrical shape and contains the cleaning water in a bottom thereof. The air inlets 52 are provided at the top surface of the housing 50, and the air outlets 54 are provided at the sidewall of the housing 50. Further, a rotation shaft 58 is installed in a central portion of the housing 50. Specifically, the rotation shaft 58 is installed such that it is inserted passing through centers of the blower unit 60, the sprinkling unit 80 and the purification unit 90.

The housing 50 further has a condensing portion 56 that is protruded from the lower ends of the air outlets 54 and is slantingly extended upward at a preset angle. By the presence of the condensing portion 56, only the purified air can be discharged from the air cleaner while the cleaning water that has reached the air outlets 54 is condensed thereby, to fall inside the housing 50 again.

The water supply unit 70 includes a water supply line 72 extended from a lower end portion of the housing 50 to an upper portion thereof; and a pump 74 installed at one side of the water supply line 72 to pump up the cleaning water so that the cleaning water is supplied to a position above the blower unit 60.

The blower unit 60 is fixedly installed at the rotation shaft 58, and serves to draw the air into the air cleaner through the air inlet 52. The blower unit 60 includes a fan main body 62 fixedly installed at a rotation shaft 58 to be rotated by a motor 69; a plurality of blades 66 formed at the outer peripheral surface of the fan main body 62 to rotate along with the fan main body 62 so as to draw the air through the air inlet 52; and a sprayer 67 formed at the fan main body 62 to spray the cleaning water into the air circulation passage. Each blade 66 is provided with a plurality of guides 68, wherein the guides 68 are elongated in a radial direction on the top surface of each blade 66. The guides 68 serves to disperse the cleaning water falling onto the top surfaces of the blades 66 in a circumferential direction of the fan main body 62.

Further, the sprayer 67 includes a water storage tub 65 concavely formed downward from the top surface of the fan main body 62, for storing therein the cleaning water falling from the water supply line 72; and a number of water jetting holes 64 provided on the peripheral surface of the water storage tub 65, for jetting the cleaning water contained in the water storage tub 65 in the circumferential direction of the fan main body 62 by a centrifugal force generated in the fan main body 62.

The sprinkling unit 80 is also fixedly installed at the rotation shaft 58 inserted therethrough, and it has a cylindrical shape with an open top. The sprinkling unit 80 includes a drum 82; a number of discharge holes 84 provided in the drum's peripheral surface; and a collection line 86 slantingly extended from the inner wall of the housing 50 to the space above the drum 82 to collect droplets into the drum 82.

As will be described in detail with reference to FIGS. 2 to 5, the purification unit 90 is submerged into the cleaning water at its lower end and is also fixedly installed at the rotation shaft 58 to rotate therewith.

Figure 2:
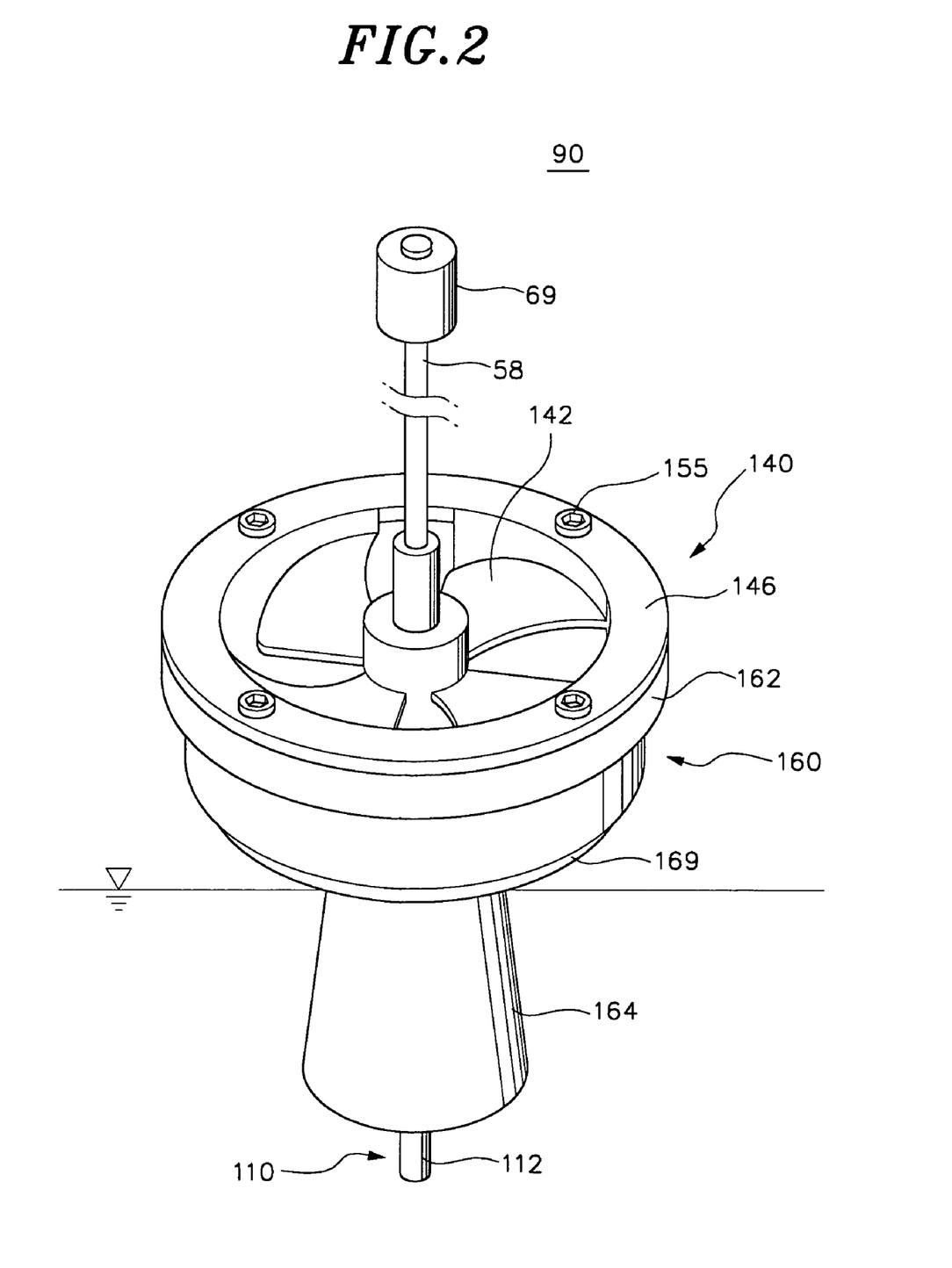
FIG. 2 describes a perspective view showing the purification unit shown in FIG. 1.
Figure 3:
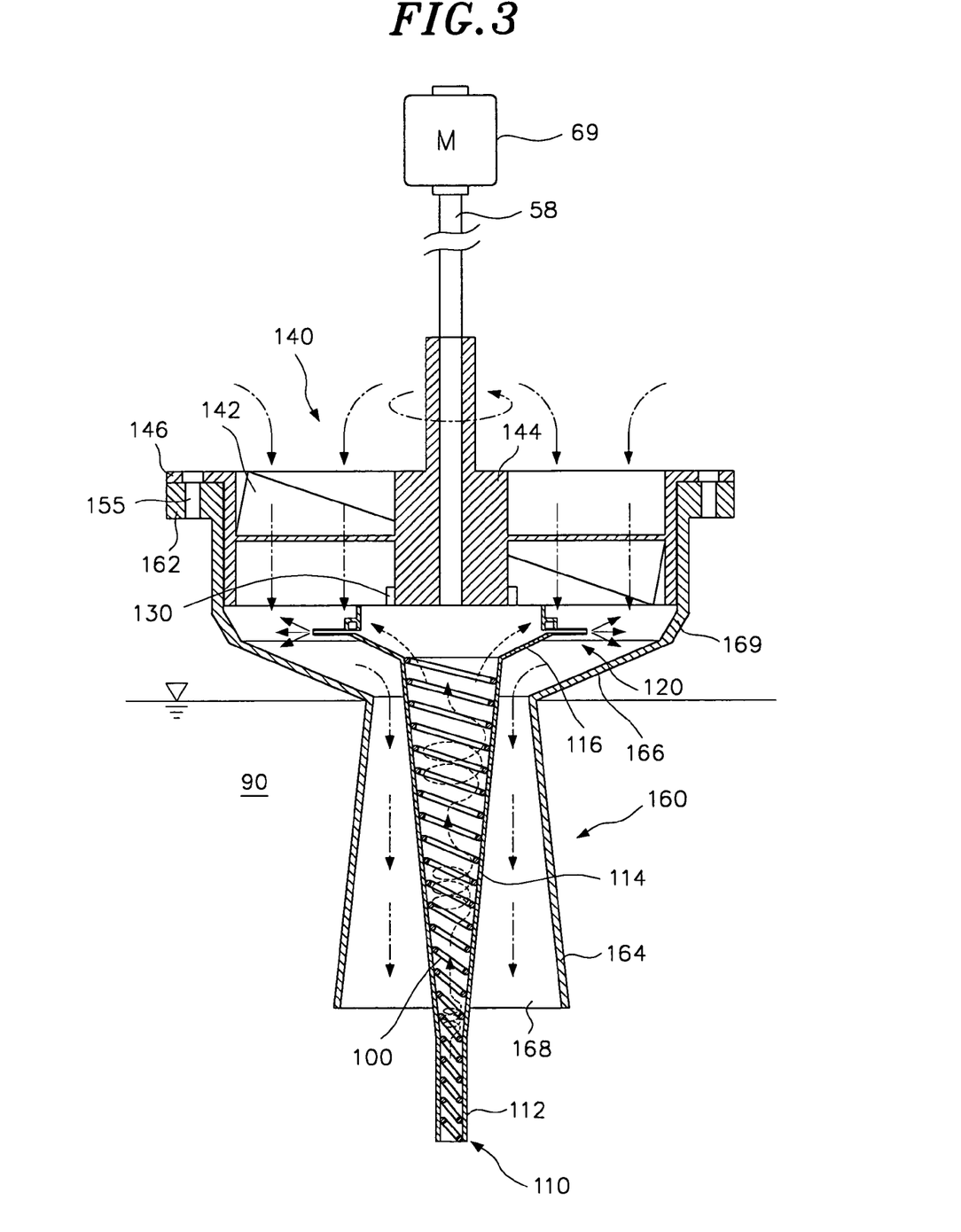
FIG. 3 provides a sectional view of a first preferred embodiment of the purification unit in accordance with the present invention.

FIG. 2 is a perspective view illustrating the purification unit shown in FIG. 1, and FIG. 3 provides a sectional view of a first preferred embodiment of the purification unit shown in FIG. 2.

As shown in FIG. 2 and FIG. 3, the purification unit 90 includes: an inner guide portion 110 whose lower end is submerged in the cleaning water, the inner guide portion 110 having a funnel shape allowing water to be upwardly transferred by a centrifugal force; a water jetting nozzle 120 connected with an upper end of the inner guide portion 110 to inject the cleaning water supplied thereto; a blower 140 installed above the water jetting nozzle 120 and fixedly installed at the rotation shaft 58, the blower 140 having a fan 142 for downwardly drawing air; and an outer guide portion 164 separately installed at an outside of the inner guide portion 110 with a gap therebetween to allow the air downwardly drawn by the blower 140 and the droplets injected from the water jetting nozzle 120 to be flow into the cleaning water.

The lower end of the inner guide portion 110 is more extended downwardly than that of the outer guide portion 160. More specifically, the lower portion of the inner guide portion 110 preferably has a funnel shape having a wide upper portion and a narrow lower portion such that the cleaning water is drawn upward by a centrifugal force while it rotates. The inner guide portion 110 is divided into three portions, a hollow introduction 112, an inner lower inclined portion 114 and inner upper inclined portion 116.

The hollow introduction 112 is formed at a lower end of the inner guide portion 110 and submerged into the cleaning water. Further, formed at an upper portion of the introduction 112 is the inner lower inclined portion 114 inclined outwardly at a predetermined angle. Formed at an upper portion of the inner lower inclined portion 114 is the inner upper inclined portion 116 having a gentle inclined angle compared to the inner lower inclined portion 114.

On an inner wall of the inner guide portion 110, a guide 100 is formed to upwardly transferring the cleaning water in a whirlpool shape. The guide 100 serves to increase an upward speed of water when the purification unit 90 rotates. The guide 100 has a spiral protrusion formed on the inner wall of the inner guide portion 110 and is preferably formed from the introduction 112 to the inner lower inclined portion 114.

The water jetting nozzle 120 is connected with an upper end of the inner guide portion 110 and is formed along a circular arc so that the cleaning water that has been upwardly transferred along the inner guide portion 110 can be injected to the outside. Further, the water discharged from the water jetting nozzle 120 is more effectively injected by a centrifugal force generated in a whirlpool shape. Accordingly, a generation of negative ions is facilitated and, further, a contact between the injected water and the air into the air cleaner increases. As a result, an adsorbing effect of contaminated substance also increases.

The blower 140 includes a fan body 144 and a circular arc shaped fan 142. The fan body 144 is fixedly inserted into a hollow engaging portion 130 through which the rotation shaft 58 is inserted, the water jetting nozzle 120 being connected to the hollow engaging portion 130. The fan 142 is installed along the fan body 144.

Further, an upper coupling unit 146 having therein a coupling hole is bent formed at a frame surrounding an outer portion of the fan 142. A lower coupling unit 162 of the outer guide portion 160, which is coupled with the upper coupling unit 146 by a screw 155, also has therein a coupling hole.

The outer guide portion 160 rotates along with the blower 140 while being coupled therewith and is separately installed at an outside of the inner guide portion 110. The outer guide portion 160 takes generally a geometric form of a beacon and is divided into several portions, i.e., an outer lower inclined portion 164, an outer upper inclined portion 166, and an upwardly inclined portion 169.

The outer lower inclined portion 164 has a reversed funnel shape having a narrow upper portion with an outlet portion 168 and a wide lower portion. That is, the outer lower inclined portion 164 is so installed as to be inwardly inclined at a predetermined angle so that a sectional area thereof becomes narrower toward an upper portion.

The outer upper inclined portion 166 is formed at an upper portion of the lower inclined portion 164 and is inclined outwardly at a predetermined angle. Further, the upwardly inclined portion 169 is slantingly installed at a side surface of the water jetting nozzle 120, so that the cleaning water can be injected from the water jetting nozzle 120 to the fan 142 after being collided with the upwardly inclined portion 169.

In the aforementioned embodiment, since the inner guide portion 110, the water jetting nozzle 120, the blower 140 and the outer guide portion 160 are connected as one unit, they rotate as integrality by an operation of the motor 69.

Hereinafter, an operation of the air cleaner in accordance with the present invention will be described.

Upon power up, the motor 69 is driven to rotate the rotation shaft 58 and in turn the blower unit 60, so that air is introduced from the air inlets 52. Thus introduced air is downward directed to the cleaning water contained in the housing 50 by the purification unit 90 after passing through the sprinkling unit 80. While the introduced air contacts the cleaning water, contaminated substances contained in the air are adsorbed by the cleaning water, and thus purified air is discharged from the air cleaner through the air outlets 54. At this time, the cleaning water is pumped up and is supplied to the position above the blower unit 60 via the water supply line 72. The cleaning water is collected in the water storage tub 65 and then dispersed through the discharge holes 64 by the rotation force to contact with the introduced air, to thereby adsorb noxious substances therefrom. Further, the cleaning water dispersed generates negative ions by colliding to the inner wall of the housing 50.

Thereafter, the cleaning water is falling downward and then is collected into the drum 82 through the collection line 86. Subsequently, the cleaning water is discharged again through the discharge holes 84, to thereby secondarily adsorb noxious substances from the air. Therefore, the efficiency of removing the contaminated substances further improves.

In addition, in the purification unit 90, the introduced air is sent downward by the blower 140 and further filtered passing through the cleaning water injected by the water jetting nozzle 120. In the meantime, the inner guide portion 110 fixed to the blower 140 by the engaging portion 130 also rotates. Consequently, the cleaning water is drawn by the introduction 112 and is outwardly injected through the water jetting nozzle 120 by a centrifugal force. When the injected water is contacted with the air that has been moved to the lower side by the fan 142 in the blower 140, bacteria, dirt or the like in the air are collected and, further, a gaseous contaminant in the air also dissolves. As a result, the air becomes clean.

At this time, since the water upwardly transferred along the inner guide portion 110 moves upwardly in a whirlpool shape through the guide 100, the centrifugal force is doubled. Accordingly, when the water is injected from the water jetting nozzle 120, a water injection level is improved, thereby effectively collecting contaminated substances such as dusts or the like in the air and also facilitating an ion generating effect.

In case the cleaning water is finely injected, a large amount of air with negative ions is generated due to the Lenard effect. The amount of air with negative ions is greater than negative ions generated by a high-pressure discharge and, also, such generated air with negative ions is close to a natural state. Moreover, the air is directed into the cleaning water in the bottom portion of the housing 50, whereby the contact between the air and the cleaning water is maximized, so that the noxious substances in the air can be removed by the cleaning water before discharged through the air outlets 54. Consequently, pleasant indoor environment can be created.

Meanwhile, the cleaning water from the water jetting nozzle 120 is dispersed after being collided with the upwardly inclined portion 169 and then mixed with the air secondarily. Since a space including the upwardly inclined portion 169 is partitioned, it is possible to minimize an outward transfer of the noise generated by the collision between the upwardly inclined portion 169 and water. Consequently, a quiet operation can be provided.

Moreover, the cleaning water that has been upwardly dispersed after being collided with the upwardly inclined portion 169 meets air thirdly by a high-speed rotation of the fan 142. Due to a friction and a static elasticity generated therebetween, contaminated substances in the air are collected by the water.

The water that has collected dusts or the like in the air falls and flows downwardly along the outer inclined portion of the outer guide portion 160.

By help of a simultaneous rotation of the outer guide portion 160 and the fan 142, air containing water flowing along the outer upper inclined portion 166 and water particles is downwardly transferred by a centrifugal force.

The air containing water and moisture that have been downwardly transferred along the outer upper inclined portion 166 is transferred toward the lower outlet portion 168 by the centrifugal force along the outer lower inclined portion 164. At this time, droplets or water particles in the air are mixed with the cleaning water in the housing and then, only clean air is raised above the cleaning water through the outlet portion 168.

As described above, in accordance with the preferred embodiment of the present invention, by contacting the air that has been downwardly transferred to clean the air with the cleaning water multiple times, contaminated substances and moisture in the air are collected by the cleaning water and then only clean air is discharged from the air cleaner, which doubles the air cleaning effect. Further, by dispersing water multiple times, the generation of the negative ions also increases.

Figure 4:
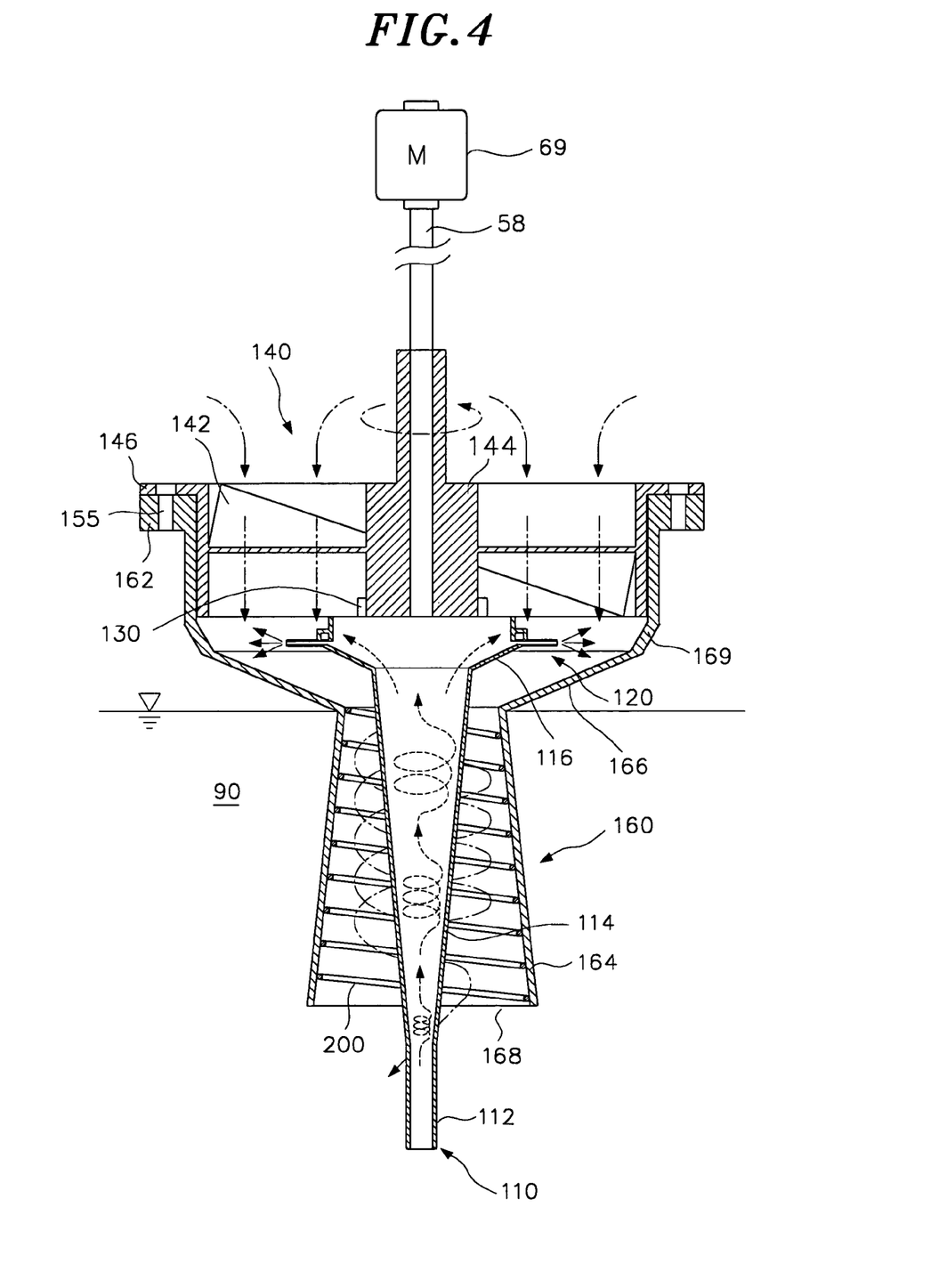
FIG. 4 represents a sectional view of a second preferred embodiment of the purification unit in accordance with the present invention.

FIG. 4 provides a sectional view of a second preferred embodiment of the purification unit shown in FIG. 2 in accordance with the present invention.

The second preferred embodiment is identical to the first preferred embodiment except that a guide 200 is formed on an inner wall of the outer lower inclined portion. Therefore, a description of the same components as those in the first embodiment will be omitted for the sake of simple explanation.

As illustrated, in comparison with the first embodiment, the second preferred embodiment of the present invention has a feature in that it has an outer guide portion for pushing air down. More specifically, the outer guide portion 160 transfers the air downwardly drawn by the blower 140 and cleaning water injected from the water jetting nozzle 120 toward the cleaning water contained in the housing 50. Further, by help of the guide 200, the air downward drawn along the outer lower inclined portion 164 is further pushed downward in a whirlpool shape, thereby increasing a downward speed of air.

Moreover, the guide 200 has a spiral protrusion formed on an inner wall of the outer guide portion 160 and is preferably formed in the lower inclined portion 164 of the outer guide portion 160.

Accordingly, the air circulation into the air cleaner can be more effectively supplied. As a result, the amount of the air to be contacted with the cleaning water per unit time increases, thereby enabling to effective adsorb dirt substances in the air.

Figure 5:
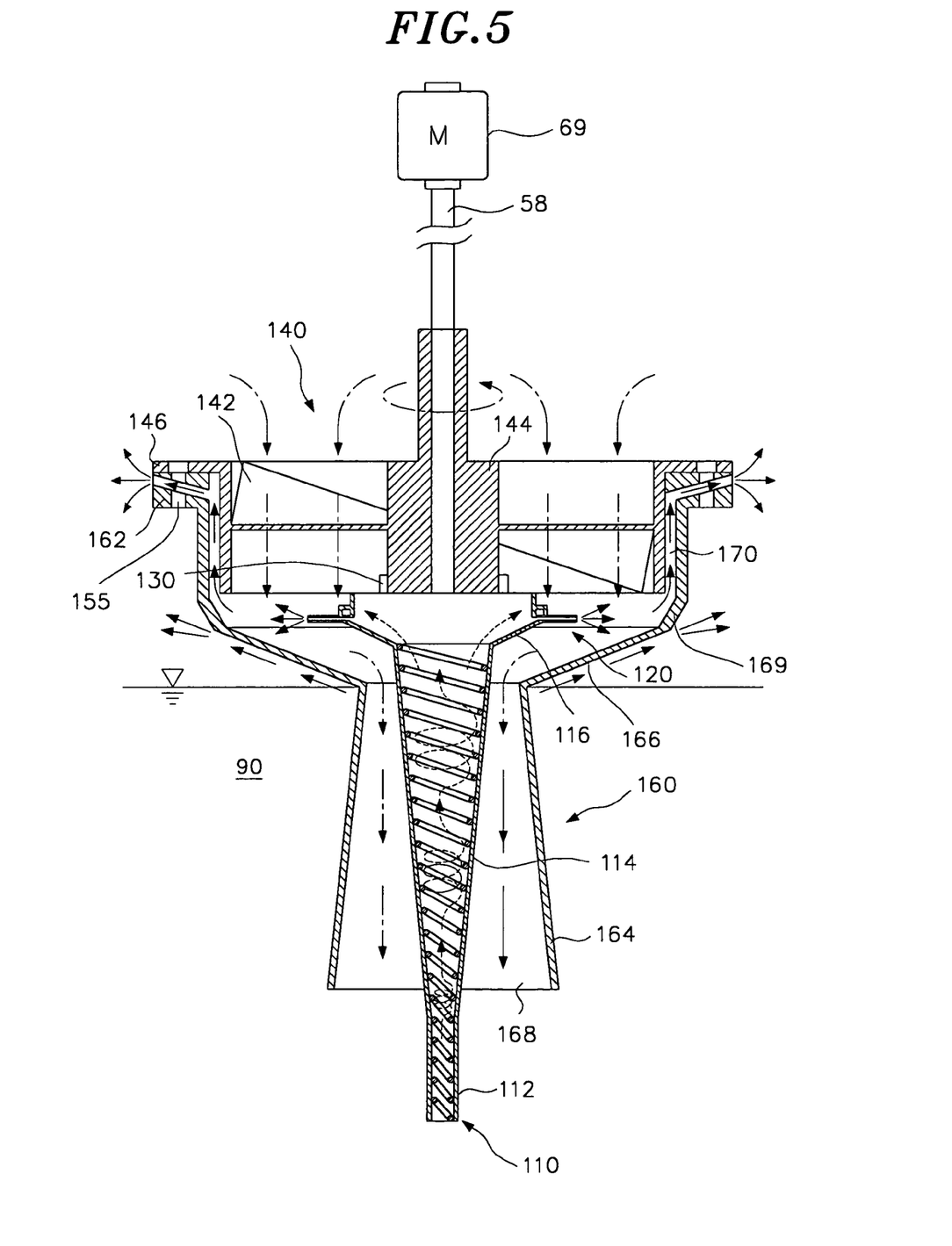
FIG. 5 offers a sectional view of a third preferred embodiment of the purification unit in accordance with the present invention.

FIG. 5 illustrates a sectional view of a third embodiment of the purification unit shown in FIG. 2 in accordance with the present invention.

The third preferred embodiment of the present invention is identical to the first embodiment except that a slit-shaped guide path 170 is formed between the blower 140 and the outer guide portion 160 and is extended over a space including the upwardly inclined portion 169. Therefore, a description of the same components as those in the first embodiment will be omitted.

In accordance with the third embodiment of the present invention, water particulars dispersed on the upwardly inclined portion 169 are upwardly transferred along the inner wall by the centrifugal force and then outwardly injected along the guide path 170.

With such additional component of the guide path 170, a contact between the air and the dispersed water is further increased.

As described above, in accordance with the embodiments of the present invention, by contacting air that has been downwardly transferred to clean the air with the dispersed water multiple times, contaminated substances and moisture in the air are collected by the cleaning water contained in the bottom of the housing and, then, only clean air is discharged from the air cleaner, which doubles the air cleaning effect. Further, by dispersing water multiple times, the generation of negative ions also increases.

Further, by stirring the cleaning water and the air with the rotation of the blower unit, the sprinkling unit and the purification unit and also by dispersing the cleaning water multiple times with a centrifugal force three times, a contact between the water particles and the air increases.

Moreover, droplets containing dirt particles are guided into the cleaning water along the outer guide portions with a clean air flow and, only clean air is discharged. Consequently, it is possible to solve a problem in which a humidity level increase above a preset level during a driving of the air cleaner and, thus, a user satisfaction can be improved.

Besides, since the cleaning water injected from the water jetting nozzle is collided with the upwardly inclined portion as an inwardly partitioned space, it is possible to minimize an outward transfer of a noise generated from the collision of the water on a wall surface. And also, since the apparatus rotates under the cleaning water, an operating noise generated during the operation may be minimized.

In addition, by forming a spiral protrusion shaped guide on an inner wall of the inner guide, an upward pushing force of the cleaning water increase.

While the invention has been shown and described with respect to the preferred embodiments, it will be understood by those skilled in the art that various changes and modification may be made without departing from the scope of the invention as defined in the following claims.

What is claimed is:

1. A wet type air cleaner, comprising:
   a housing provided with an air inlet and an air outlet and containing cleaning water therein;
   a motor having a rotation shaft to provide rotation force; and
   a purification unit fixedly installed to the rotation shaft, wherein the purification unit includes:
   an inner guide portion whose introduction is submerged into the cleaning water in the housing, for drawing upwardly the cleaning water, the inner guide portion having a guide formed on an inner wall of the inner guide portion for upward drawing of the cleaning water;
   a water jetting nozzle connected to an upper end of the inner guide portion for injecting the cleaning water drawn thereto through the inner guide portion;
   a blower installed at upper end of the water jetting nozzle, the blower having a fan for drawing air downward; and
   an outer guide portion separately installed at an outside of the inner guide portion with a gap therebetween to allow the air downwardly drawn by the blower and the cleaning water injected from the water jetting nozzle to flow into the cleaning water.

2. The wet type air cleaner of claim 1, wherein the inner guide portion and the outer guide portion rotate along with the blower.

3. The wet type air cleaner of claim 1, wherein the inner guide portion has a funnel shape having a wide upper portion and a narrow lower portion.

4. The wet type air cleaner of claim 1, wherein the outer guide portion has a geometric form of a beacon.

5. The wet type air cleaner of claim 4, wherein a lower portion of the outer guide portion has a reversed funnel shape having a narrow upper portion and a wide lower portion.

6. The wet type air cleaner of claim 1, wherein a lower end of the introduction is more extended downwardly than that of the outer guide portion so that the inner guide portion is submerged into the cleaning water in the housing.

7. The wet type air cleaner of claim 1, wherein the guide in the inner guide portion is a spiral protrusion.

8. The wet type air cleaner of claim 1, further comprising a guide path formed between the blower and the outer guide portion and extended over a space of the housing, for guiding water particulars dispersed by the water jetting nozzle upwardly.

9. A wet type air cleaner, comprising:
   a housing provided with an air inlet and an air outlet and containing cleaning water therein;
   a motor having a rotation shaft to provide rotation force; and a purification unit fixedly installed to the rotation shaft, wherein the purification unit includes:

an inner guide portion whose introduction is submerged into the cleaning water in the housing, for upwardly drawing the cleaning water;

a water jetting nozzle connected to an upper end of the inner guide portion for injecting the cleaning water drawn thereto through the inner guide portion;

a blower installed at upper end of the water jetting nozzle, the blower having a fan for drawing air downward;

an outer guide portion separately installed at an outside of the inner guide portion with a gap therebetween to allow the air downwardly drawn by the blower and the droplets injected from the water jetting nozzle to flow into the cleaning water, the outer guide portion having a guide formed on an inner wall thereof for downward drawing of the air from the blower.

10. The wet type air cleaner of claim 9, wherein the inner guide portion and the outer guide portion rotate along with the blower.

11. The wet type air cleaner of claim 9, wherein the inner guide portion has a funnel shape having a wide upper portion and a narrow lower portion.

12. The wet type air cleaner of claim 9, wherein the outer guide portion has a geometric form of a beacon.

13. The wet type air cleaner of claim 12, wherein a lower portion of the outer guide portion has a reversed funnel shape having a narrow upper portion and a wide lower portion.

14. The wet type air cleaner of claim 9, wherein a lower end of the introduction is more extended downwardly than that of the outer guide portion so that the inner guide portion is submerged into the cleaning water in the housing.

15. The wet type air cleaner of claim 9, wherein the guide in the outer guide portion is a spiral protrusion.

16. The wet type air cleaner of claim 9, further comprising a guide path formed between the blower and the outer guide portion and extended over a space of the housing, for guiding water particulars dispersed by the water jetting nozzle upwardly.

* * * * *